US012765780B2

(12) United States Patent
Zahner et al.

(10) Patent No.: US 12,765,780 B2
(45) Date of Patent: Oct. 20, 2026

(54) SENSOR UNIT FOR A PORTABLE COMPUTER SYSTEM AND INTEGRATION OF THE SENSOR UNIT

(71) Applicant: greenTEG AG, Ruemlang (CH)

(72) Inventors: Michele Zahner, Zürich (CH); Thomas Helbling, Frauenfeld (CH); Lukas Durrer, Ebnat-Kappel (CH); Etienne Schwyter, Zürich (CH)

(73) Assignee: greenTEG AG, Ruemlang (CH)

( * ) Notice: Subject to any disclaimer, the term of this patent is extended or adjusted under 35 U.S.C. 154(b) by 436 days.

(21) Appl. No.: 18/232,067

(22) Filed: Aug. 9, 2023

(65) Prior Publication Data

US 2023/0389804 A1 Dec. 7, 2023

Related U.S. Application Data

(62) Division of application No. 16/470,877, filed as application No. PCT/EP2017/082994 on Dec. 15, 2017, now Pat. No. 11,759,111.

(30) Foreign Application Priority Data

Dec. 21, 2016 (CH) ...................................... 1695/16

(51) Int. Cl.

*A61B 5/01* (2006.01)
*A61B 5/00* (2006.01)
(Continued)

(52) U.S. Cl.

CPC .............. *A61B 5/01* (2013.01); *A61B 5/0008* (2013.01); *A61B 5/681* (2013.01); *G01K 1/165* (2013.01);
(Continued)

(58) Field of Classification Search

CPC ......... A61B 5/01; A61B 5/0008; A61B 5/681; A61B 2562/0271; A61B 5/6833;
(Continued)

(56) References Cited

U.S. PATENT DOCUMENTS 5,816,706 A 10/1998 Heikkila
8,708,926 B2 4/2014 Grassl et al.
(Continued)

FOREIGN PATENT DOCUMENTS

DE 10038247 A1 * 5/2001 .............. G01K 7/42
DE 102005004933 B3 8/2006
(Continued)

OTHER PUBLICATIONS

R. G. Haahr et al., "An Electronic Patch for Wearable Health Monitoring by Reflectance Pulse Oximetry," in IEEE Transactions on Biomedical Circuits and Systems, vol. 6, No. 1, pp. 45-53, Feb. 2012 (Year: 2012).*
(Continued)

*Primary Examiner* — John E Breene
*Assistant Examiner* — Manuel Salvador Castellon, Jr.
(74) *Attorney, Agent, or Firm* — BLANK ROME LLP

(57) ABSTRACT

A sensor unit determines the core body temperature by means for measured values which can be determined outside the body on a surface. The unit has at least one heat flow sensor, and at least one temperature sensor, which allows optimized determination of the core body temperature. The sensor unit includes at least one monolithic heat flow sensor in the form of a sandwich-like structure with multiple layers of different materials and at least one temperature sensor, which are soldered onto a circuit board at a distance from one another or onto the circuit board at the same height along a longitudinal direction of the circuit board, wherein the sensors are connected to an analog-to-digital converter
(Continued)

and a microcontroller via wires or strip conductors. The electronic components can be connected to the electronics of a portable computer system.

22 Claims, 6 Drawing Sheets

(51) Int. Cl.
*G01K 1/16* (2006.01)
*G01K 13/20* (2021.01)

(52) U.S. Cl.
CPC ...... *G01K 13/20* (2021.01); *A61B 2562/0271* (2013.01)

(58) Field of Classification Search
CPC ........ A61B 2562/0276; A61B 2562/12; G01K 1/165; G01K 13/20; G01K 1/143; G01K 1/16; G04G 17/00; G04G 17/04; G06F 1/1684; G06F 1/163
See application file for complete search history.

(56) References Cited

U.S. PATENT DOCUMENTS

| | | | | |
|---|---|---|---|---|
| 11,051,700 | B2 | 7/2021 | Koch et al. | |
| 2004/0039254 | A1 | 2/2004 | Stivoric | |
| 2005/0245839 | A1* | 11/2005 | Stivoric | A61B 10/0012 374/E1.004 |
| 2006/0056487 | A1 | 3/2006 | Kuroda | |
| 2007/0100666 | A1 | 5/2007 | Stivoric et al. | |
| 2010/0121217 | A1 | 5/2010 | Padiy | |
| 2010/0183044 | A1 | 7/2010 | Tanaka | |
| 2010/0268113 | A1 | 10/2010 | Bieberich | |
| 2012/0114013 | A1 | 5/2012 | Tsuchida | |
| 2012/0128024 | A1 | 5/2012 | Tsuchida | |
| 2012/0165759 | A1 | 6/2012 | Rogers | |
| 2013/0098150 | A1 | 4/2013 | Sella | |
| 2015/0257652 | A1 | 9/2015 | Van Duren | |
| 2016/0069752 | A1* | 3/2016 | Shimizu | G01K 13/20 600/549 |
| 2016/0081629 | A1 | 3/2016 | Rostalski et al. | |
| 2016/0313193 | A1 | 10/2016 | Nakagawa | |
| 2017/0112391 | A1* | 4/2017 | Stivoric | A61B 5/0022 |

FOREIGN PATENT DOCUMENTS

| | | | | |
|---|---|---|---|---|
| DE | 102015206938 | | 10/2016 | |
| EP | 2251660 | B1 | 5/2009 | |
| JP | 2005536260 | A * | 12/2005 | A61B 5/256 |
| WO | WO-02/078538 | A2 | 10/2002 | |
| WO | WO-2005/092177 | A1 | 10/2005 | |
| WO | WO-2014/177263 | A1 | 11/2014 | |

OTHER PUBLICATIONS

International Search Report for PCT/EP2017/082994, dated Feb. 16, 2018, 3 pages.

"Simplified Heat Flow Measurement: Construction & Principle of Operation", RDF; https://web.archive.org/web/20030401070308/http://www.rdfcorp.com/anotes/pa-hfs/pa-hfs_02.shtml, Apr. 2003; 2 pages.

* cited by examiner

SENSOR UNIT FOR A PORTABLE COMPUTER SYSTEM AND INTEGRATION OF THE SENSOR UNIT

RELATED APPLICATIONS

This application is a divisional application of U.S. patent application Ser. No. 16/470,877, filed on Jun. 18, 2019, which is a national phase of PCT/EP2017/082994, filed on Dec. 15, 2017, which claims the benefit of Swiss Application No. 1695/16, filed on Dec. 21, 2016. The entire contents of these applications are hereby incorporated by reference.

TECHNICAL FIELD

The present invention describes a sensor unit for determining the core body temperature by means of measured values, which can be determined outside the body on a surface, comprising at least one heat flow sensor and at least one temperature sensor, a portable computer system with a sensor unit, and the manufacture of a sensor unit comprising at least one measuring sensor and electronic components on a printed circuit board, and the integration of the sensor unit into a housing of a portable computer system, or into an adhesive pad for attachment onto the skin.

PRIOR ART

Portable technical data processing devices with measuring capabilities are of known art in various configurations, with or without a housing, as parts of clothing, or in the form of jewellery. These portable computer systems or wearable computers are the subject matter of the research field "wearable computing". The wearable computers or portable computer systems have at least one sensor unit, with which data is collected via at least one sensor from the real world. The measured data is then either processed in the portable computer system itself or transferred to another computer, in particular to a smart phone. The user can view the recorded data and process it further. The portable computer system comprises a housing, in which a sensor unit and electronics are integrated. As a rule the electronics have at least one microcontroller and one read-out/storage unit, which are connected to the sensor unit.

One example of a wearable computer, or portable computer system, is an activity tracker, also called a fitness or health armband, smart band, or fitness tracker. Using software operated in the electronics, data from at least one sensor of the sensor unit are collected, further processed, stored in a memory as necessary, and/or forwarded to a smart phone. Accordingly, data relevant to fitness and health, such as running distances, energy consumption, and also, in some cases, heart rate, body temperature, oxygen content in the blood, or sleep quality, can be determined.

Here the determination of the internal body temperature, or core body temperature, by means of a portable computer system is of interest. The non-invasive and continuous determination of internal body temperature, as measured on the skin, is important for patient monitoring in hospitals, for the prevention of heat stroke in athletes, or for the determination and monitoring of the circadian cycle for the diagnosis of sleep disorders and other illnesses.

In the simplest case, the sensor unit of the portable computer system is based on a temperature sensor to determine the skin temperature in combination with thermal insulation over the sensor and its surroundings. The purpose of the insulation is to keep the skin temperature as close as possible to the core body temperature. In many cases the method is inaccurate and unsuitable for use under changing external conditions.

To improve the measurement of the core body temperature, the sensor unit of the portable computer system may include a so-called double temperature sensor, as recorded in DE10038247. Here two temperature sensors are separated from one another by a thermal insulator with a known thermal resistance. In most cases this method requires a calibration measurement so as to determine the thermal resistance, which depends on the person and also the location of the measurement.

The double sensor method has multiple disadvantages. One severe problem is represented by the thermal parasitic heat losses between the two temperature sensors, which can lead to strong deviations. These must be resolved by thermal insulation and by complex compensation algorithms, as described in DE102005004933. Another disadvantage lies in the size of the system. In order to achieve good sensitivity, the temperature difference in application must be sufficiently large, which means that the material between the two temperature sensors must have a certain minimum thickness. This makes the sensor system rather chunky and bulky and less suitable for ease of integration into housings of prior art.

The sensor units of known art for determining the core body temperature are not yet suitable for ease of integration into the housing of a portable computer system. In order to avoid parasitic heat losses, thermal insulators and additional structures are required, resulting in a complex design, and making it difficult to integrate the sensor unit into the housing of a portable computer system. A further disadvantage is the measurement inaccuracy of the sensor units of known art when determining the core body temperature.

WO02078538 presents the determination of the core body temperature with the aid of a heat flow sensor, which is attached to the skin of a user. The heat flow sensor forms part of a sensor unit, which here too must be attached in a complex manner to a computer system. In WO2005092177 another sensor unit is described that is suitable for the measurement of the core body temperature, which comprises, amongst other items, a heat flow sensor, and can likewise be connected to a portable computer system. This has brought us closer to the goal of determining the core body temperature as accurately as possible, but the manufacture of the sensor unit and the integration of the sensor unit in the portable computer system remains complicated and cumbersome.

PRESENTATION OF THE INVENTION

The object of the present invention is that of creating a compact sensor unit that can easily be installed, either for installation in a portable computer system, or for mounting on or in an adhesive pad, which allows an optimised determination of the core body temperature.

An opportunity is created, by which to simplify the manufacture of the sensor unit, and to simplify the attachment of the sensor unit onto or into a housing of a portable computer system, or onto or into an adhesive pad.

With the sensor unit as presented thermophysiological data on a body, especially the internal body temperature, or core body temperature, can be measured, whereby heat flows and surface temperatures are determined. Other parameters can be: the heat output of the skin, calorie consumption, calorie intake, blood pressure, blood sugar, internal temperature at a particular point on the body, compensated skin temperature, etc.

In particular, a method is described that allows the coupling of a sensor unit to a housing of a portable computer system, or its attachment onto or into an adhesive pad, or by means of a tape, with a few operative steps.

BRIEF DESCRIPTION OF THE FIGURES

Further features, details and advantages of the invention ensue from the following description of preferred embodiments of the invention, together with the figures. Here:

FIG. 4*a* shows a plan view onto the sensor unit shown in FIG. 3 after attachment of the sensor unit sleeve, while

FIG. 6*a* shows a schematic cross-sectional view of the fixation of a sensor unit to a housing, while

FIG. 7*a* shows a schematic cross-sectional view of a first step of a manufacturing method for a sensor unit, while

DESCRIPTION

Figure 1A:
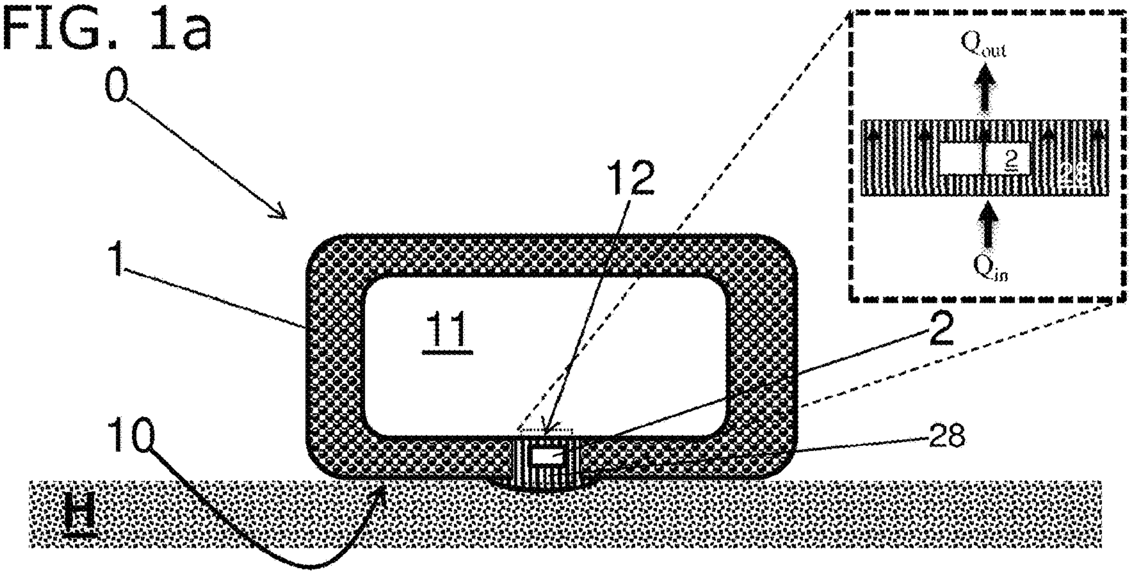
FIGS. 1*a* to 1*c* show schematic cross-sectional views of portable computer systems with integrated sensor units.

A portable computer system 0 is here represented in the form of an armband having a hollow interior 11 with a housing 1. The housing 1 is laid, with a skin contact side 10, onto the skin H of a user. A heat flow occurs from the body of the user, across the skin H, crossing the housing 1 of the portable computer system 0, into the interior 11; in the detail of FIG. 1*a* the heat flow through the housing 1 is marked as $Q_{in}$ to $Q_{out}$. People and animals are possible users.

A sensor unit 2, which is specified in more detail below, is inserted into the housing 1, detachably or non-detachably attached, and electrically connected to the electronics (not shown) of the portable computer system 0. The sensor unit 2 is at least partially surrounded by a sensor unit sleeve 28 and is pressed into the housing 1, that is to say, it is bonded in with adhesive, or encapsulated. The sensor unit sleeve 28 is manufactured from a thermally conductive material, in particular silicone. By using a material with a similar thermal conductivity to that of the heat flow sensor itself, as described later, it is possible to homogenise the heat flow and thus minimise parasitic heat flows. Furthermore, a good thermal conductivity means that the temperature measured is closer to the skin temperature. The conductivity of the sensor unit sleeve 28 in our case should lie between 0.3 and 10 W/mK; optimally between 0.8 and 3 W/mK. For metrological reasons, the sensor unit 2 should be located as close as possible to the user's skin, but in principle can be arranged anywhere in the heat path.

In the embodiment as shown in FIG. 1*a* a through hole 12 is provided, which crosses the housing 1 completely, into which a completely encapsulated sensor unit 2 is inserted. The sensor unit sleeve 28 protrudes slightly from the through hole 12 and from the skin contact side 10, and when in use comes into contact with the skin H of the user. The heat flow from the skin H, and thus from the body, via the skin, through the sensor unit sleeve 28 and the sensor unit 2, adjusts itself during use, and can be used to determine the core body temperature.

Figure 1B:
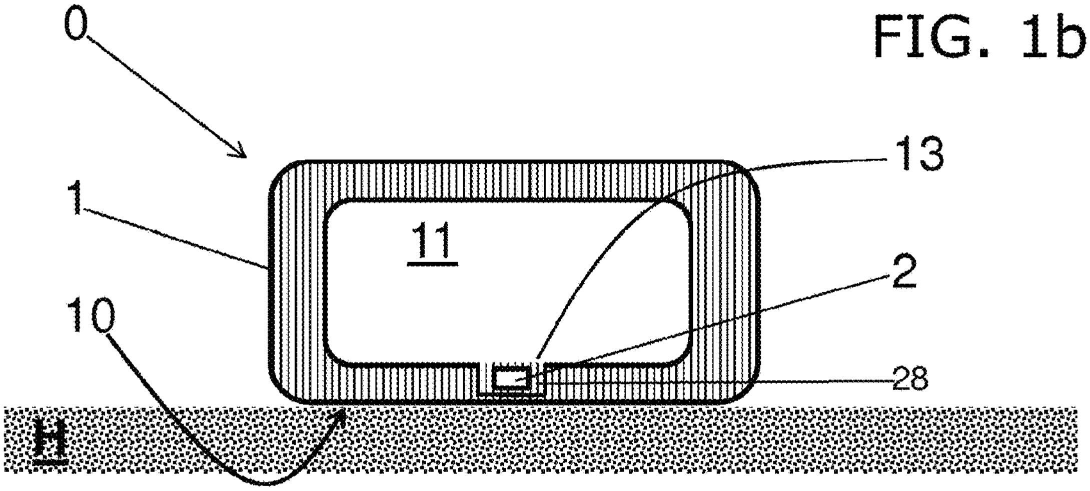

As shown in FIG. 1*b*, a cavity in the form of a blind hole 13 can also be arranged in the housing 1 of the portable computer system, into which the sensor unit 2 with a partially surrounding sensor unit sleeve 28 is introduced. Here too the sensor unit 2 including the sensor unit sleeve 28 is inserted into the blind hole 13 in the form of a plug, and is thus detachably connected to the housing 1.

Figure 1C:
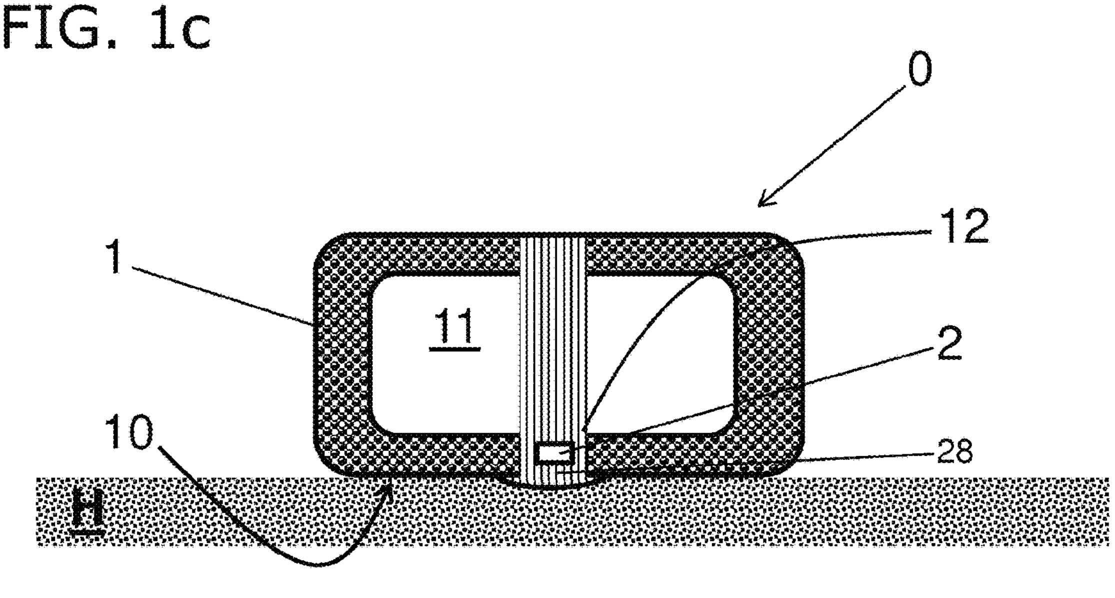

To increase the stability of the mounting of the sensor unit 2 with the sensor unit sleeve 28 in the housing 1, the sensor unit sleeve 28 can extend across the housing 1, as shown in FIG. 1*c*. This creates a thermal path such that the thermal equilibrium between the environment and the body adjusts itself as quickly as possible. Accordingly, the sensor unit sleeve 28 extends from the skin contact side 10 to a side of the housing 1 remote from the skin contact side 10, and thereby crosses the housing 1.

FIGS. 2*a* to 2*d* show embodiments of the sensor units 2 for determining the core body temperature. The aim is to create a sensor unit 2 that is as compact as possible, mechanically robust, and in the best case is flexibly configured.

The basis of the sensor unit 2 is a printed circuit board 22, onto which at least one heat flow sensor 20 and at least one temperature sensor 21 are soldered. The printed circuit board 22 can be executed in a rigid or flexible manner, and, in addition to strip conductors made from an electrical conductor, comprises insulating material, preferably a fibre-reinforced plastic. Optimally, the material of the at least one printed circuit board 22 has a thermal conductivity of between 0.3 and 10 W/mK, and preferably between 0.8 and 3 W/mK, such that a homogeneous heat flow is guaranteed.

The various sensors 20, 21 are placed on soldering surfaces on the printed circuit board 22 and attached with solder. The at least one heat flow sensor 20 and the at least one temperature sensor 21 are arranged spaced apart from one another along a longitudinal direction. The heat flow sensor 20 and the temperature sensor 21 are attached onto the same side of the printed circuit board 22.

Other components, in particular blocks made from thermally insulating materials 23 and thermal capacitances 24, are also attached onto the printed circuit board 22. The thermal insulator 23 and the thermal capacitance 24 are bonded to the printed circuit board 22 with an adhesive such as an acrylic, epoxy or polyurethane or, if the material permits, are soldered on.

In order to keep the thermal transfer resistance between components as low as possible, for example between the heat flow sensor 20 and the thermal capacitance 24, a thermally conductive adhesive should be used in the case of adhesive bonding.

Electronic components such as an analogue-to-digital converter 25, a microcontroller 26, and a read-out/storage unit 27, can also be attached onto the printed circuit board 22 in an electrically conductive manner. To achieve sufficiently high measurement signals, however, it is sufficient to attach only the analogue-to-digital converter 25 onto the printed circuit board 22, and to arrange the microcontroller 26 and the read-out/storage unit 27 at a distance from the printed circuit board 22 by means of wires or so-called flex-rigid printed circuit boards, a layered arrangement of plastic and copper layers, which form a flexible composite printed circuit board.

Connecting wires 3 are arranged leading away from the printed circuit board 22; these transmit the measured signals, or processed signals, to the electronics of the portable computer system 0. Optionally, the connecting wires 3 can also be formed by flexible printed circuit boards or strip conductors, to which the electronic components can be connected.

In order to increase the stability of the sensor unit 2 and to achieve a homogeneous heat flow, the printed circuit board 22, populated with the components, is at least partially surrounded by the sensor unit sleeve 28. While the variants shown in FIGS. 2*a* and 2*d* show a sensor unit 2 completely encapsulated in a sensor unit sleeve 28, the other embodiments here are only provided with a sensor unit sleeve 28 on their side of the sensor unit 2 that subsequently faces towards the skin H.

The sensor unit sleeve 28 does not necessarily have to consist of only one material. For example, a silicone that is more compatible with the skin can be arranged adjacent to the skin, and a thermally conductive silicone can then be applied up to the printed circuit board 22. The printed circuit board 22 itself has a thermal conductivity that is similar to that of the sensor unit sleeve 28. Above the printed circuit board 22 there is another 0.5 cm of thermally conductive silicone, and then a metal rod, or a silicone-filled metal rod, up to the top of the housing. Tests have shown that it does not matter whether the at least one heat flow sensor 20 and the at least one temperature sensor 21 are located on the same side of the printed circuit board 22, or on opposite sides. The measurements of the heat flow, using the heat flow sensor 20, and the temperature, using the temperature sensor 21, are used to determine the actual core body temperature.

Figure 2A:
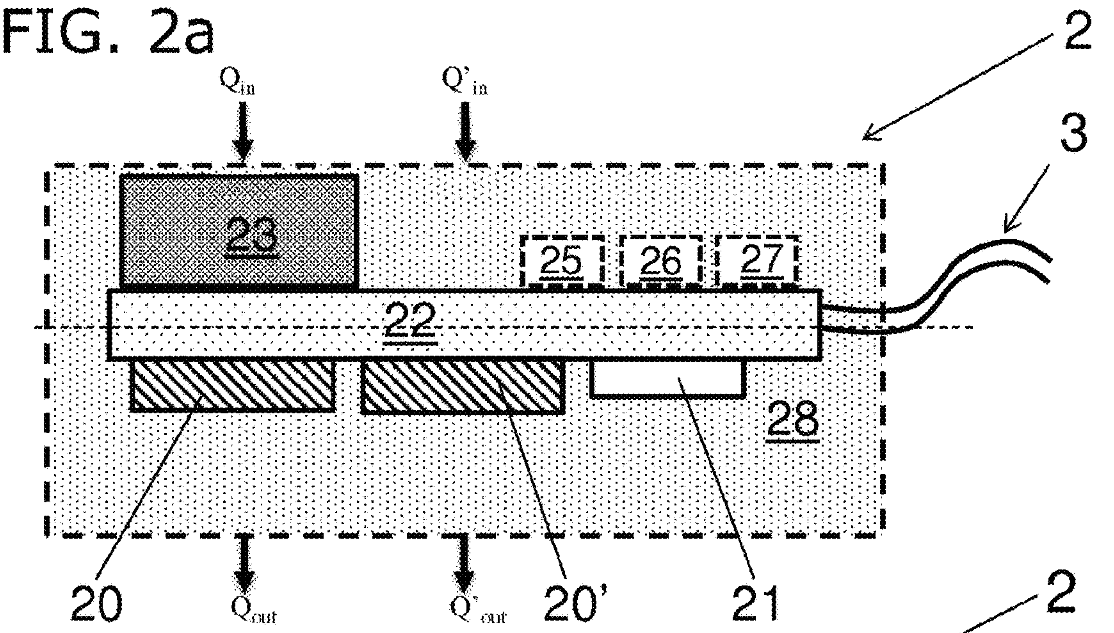
FIGS. 2*a* to 2*e* show schematic cross-sectional views of various sensor units.
Figure 2B:
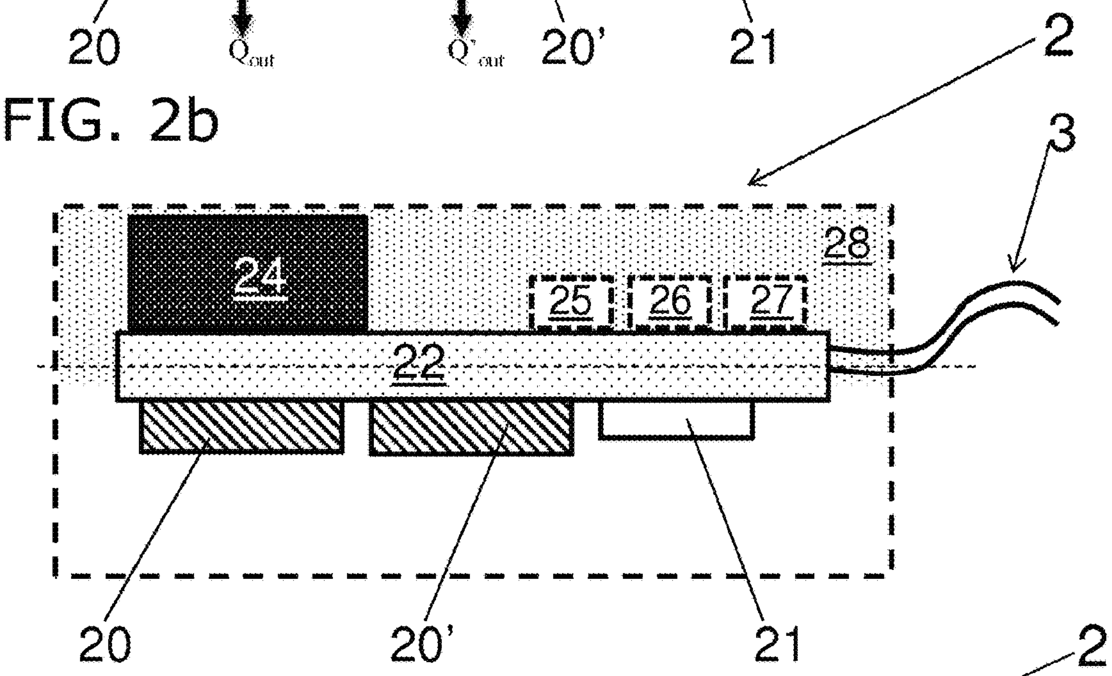

In FIG. 2*a* the sensor unit 2 has two heat flow sensors 20, 20' and one temperature sensor 21, soldered to the skin-facing side of the printed circuit board 22. Here a thermal insulator 23 is attached, at the height in the longitudinal direction of a heat flow sensor 20, on the side of the printed circuit board 22 that is free of heat flow sensors. In the variant shown in FIG. 2*b*, a thermal capacitance 24 is attached, at the height in the longitudinal direction of a heat flow sensor 20, on the side of the printed circuit board 22 that is free of heat flow sensors. In this manner a heat flow is measured through a first heat flow sensor and a thermal insulator 23, or a thermal capacitance 24, as is a heat flow through a second heat flow sensor The two measured values, together with the measurement of the temperature by means of the temperature sensor 21, enter into the determination of the core body temperature. In accordance with a prior calibration of the heat flow sensor measurement with and without the thermal insulator 23 or the thermal capacitance 24, the determination of the core body temperature can be optimised.

The thermal insulator 23 has a high thermal resistance, whereby the thermal conductivity A of the material of the thermal insulator 23 is very low. As shown in FIG. 2*a*, the heat flow through the first heat flow sensor 20 differs from the heat flow through the second heat flow sensor 20' by virtue of the thermal insulator 23. A foamed plastic material is used as the thermal insulator 23, whereby the heat flow through the first heat flow sensor 20 is less than that through the second heat flow sensor 20'. The decisive factor is the difference between the two heat flows, from which the core body temperature can be better determined, with the aid of an algorithm. This design ensures that the sensor unit 2 is more robust with respect to changes in the thermal coupling between the sensors 20, 20', 21, 21' and the skin H. The heat flow difference is taken into account in the determination, for which reason the properties of the thermal insulator 23 must be known and experimentally determined and calibrated. The thermal conductivity λ of the thermal insulator material 23 should be of the order of that for air ($\lambda_{air}$=0.024 W/m/K), i.e. between 0.01 W/m/K and 0.1 W/m/K.

Materials for the sensor unit sleeve 28 can include polymers such as polypropylene, PES, PE, PET, polyethylene, acetal, nylon, polybutylene terephthalate, polysulfone, PPS, polycarbonate, Teflon, polyester, PMMA, PSU, PEEK, TPE, TPU, parylene or PTFE. Ethylene-propylene-diene rubber (EPDM) and polypropylene have preferably been chosen. The at least one printed circuit board 22, that is to say, the material of the printed circuit board 22, can also be part of the sensor unit sleeve 28. FR-4 or FR4, a composite material of epoxy resin and glass fibre fabric, can, for example, be used as the material for the printed circuit board 22. As of known art to the person skilled in the art, the thermal conductivity of the materials can be improved or adapted by a specialised form of manufacture (e.g. by the addition of particles) such that the material has a similar thermal conductivity to that of the sensor unit itself.

Accordingly, the thermal capacitance 24 has a very low thermal resistance and the material has a very high thermal conductivity, that is to say, a very high value of λ. The thermal capacitance 24 should absorb the heat to the maximum extent. Here too, the heat flow through the first heat flow sensor 20 differs from the heat flow through the second heat flow sensor 20'. Thermally conductive silicone has been successfully used as the material. However, metals can also be used. The thermal conductivity λ of the material of the thermal capacitance 24 should be significantly higher than the thermal capacitance of air ($\lambda_{air}$=0.024 W/m/K), i.e. greater than 0.1 W/m/K.

The thermal insulator 23 and the thermal capacitance 24 are attached to the printed circuit board 22 with a suitable adhesive. If copper or brass is used, this can be soldered onto the printed circuit board 22.

Figure 2C:
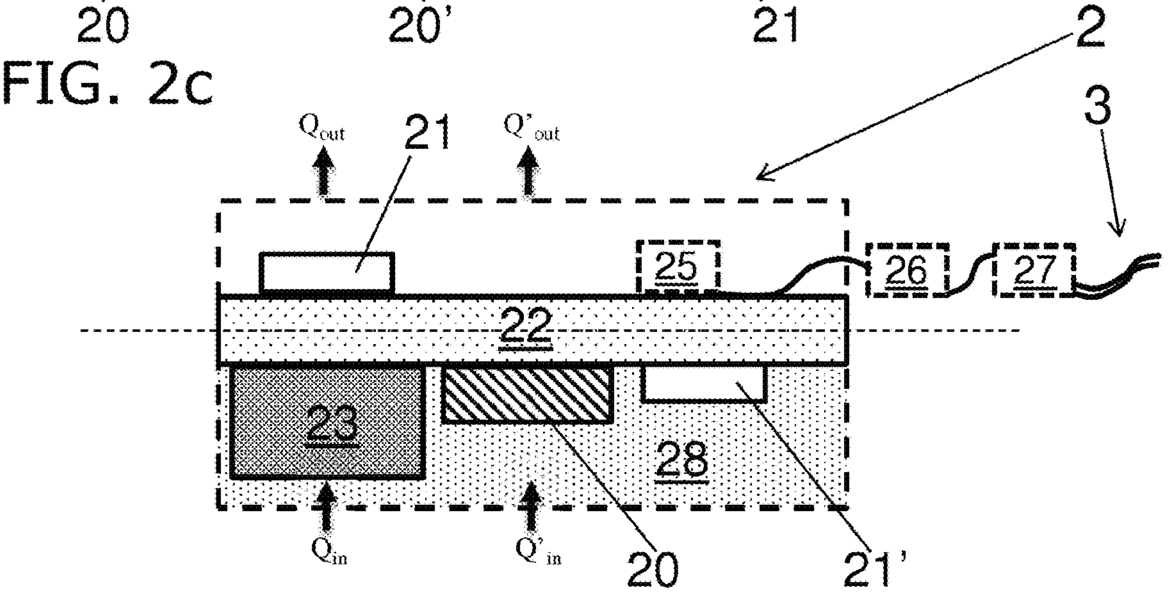
Figure 2D:
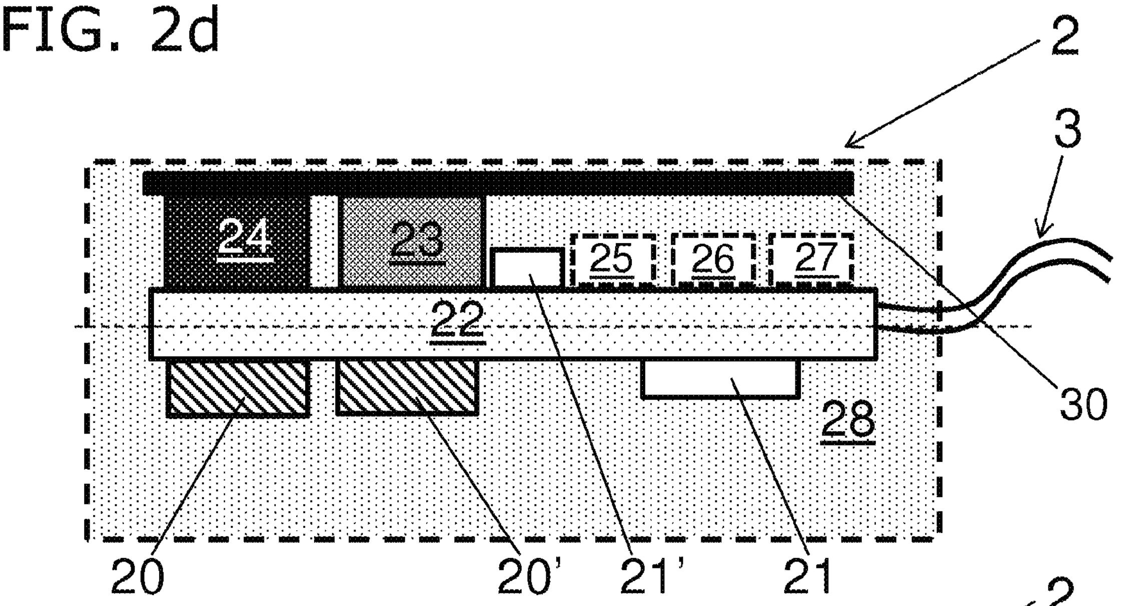
Figure 2E:
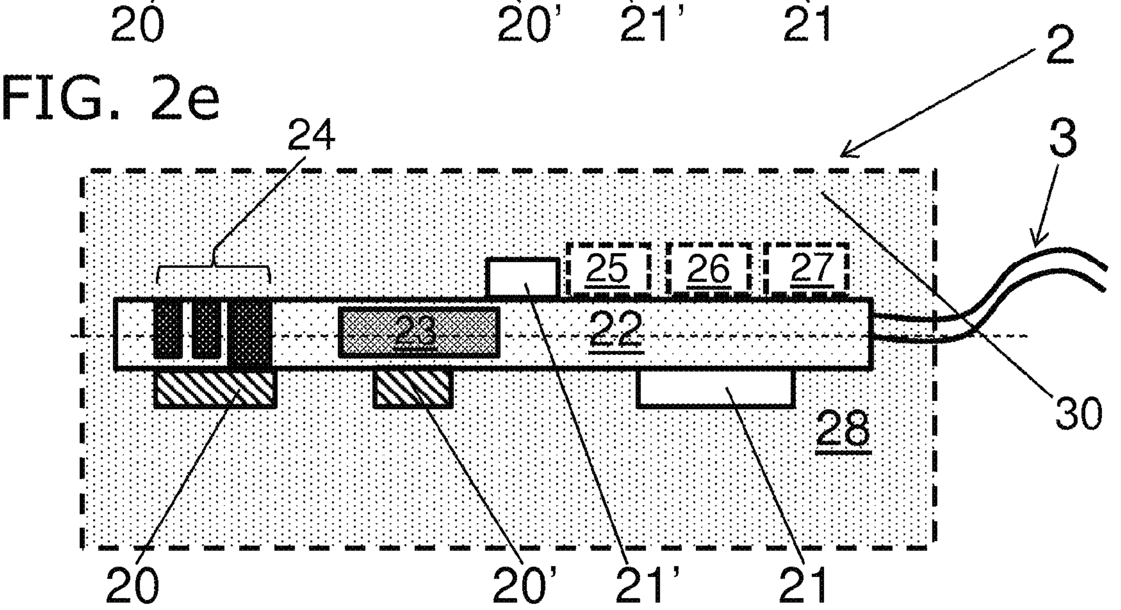

The variant depicted in FIG. 2*c* shows a heat flow sensor 20 and two temperature sensors 21, 21', whereby a thermal insulator 23 is attached onto the heat flow sensor side of the printed circuit board 22, which is located opposite the temperature sensor 21' at the same height in the longitudinal direction of the printed circuit board 22. The temperature sensor 21 is connected directly to the printed circuit board 22, but is spaced apart from the thermal insulator 23. This allows two different temperature measurements by means of the two temperature sensors 21, 21' arranged at a distance from one another in the longitudinal and transverse directions.

The electronic components of the sensor unit 2, the at least one heat flow sensor 20, the at least one temperature sensor 21, the analogue-to-digital converter 25, the microcontroller 26 and the read-out/storage unit 27, encapsulated in an integrated circuit 29 (IC), can be aggregated in a chip housing, and, together with the printed circuit board 22, form the sensor unit 2. In practice, the encapsulation is achieved either by the application of adhesive to both sides, or by a casting process. The integrated circuit 29, that is to say, the chip housing, is soldered onto the printed circuit board 22. By virtue of the compact design of the integrated circuit 29, the manufacture of the sensor unit 2 can be simplified even further.

FIG. 2*d* shows a sensor unit 2, whereby the two heat flow sensors 20, 20' are soldered onto the same side of the at least one printed circuit board 22, spaced apart from one another in the longitudinal direction. A thermal capacitance 24 is arranged on the side of at least one printed circuit board 22 that is free of heat flow sensors, at the height of the first heat flow sensor 20 in the longitudinal direction. In addition, a thermal insulator 23 is arranged on the side of the at least one printed circuit board 22 that is free of heat flow sensors, at the height of the second heat flow sensor 20' in the longitudinal direction. On the side that is free of heat flow sensors, a metal plate 30 is arranged so as to be in contact with the thermal insulator 23 and the thermal capacitance 24, and running parallel to the printed circuit board 22. The metal plate 30 can also be arranged so as to be in contact with, and/or partially covering, a block made from a thermally conductive material on the printed circuit board 22, or the sensor unit sleeve 28. By means of the metal plate 30, which is preferably made from aluminium and can be rigid or flexible, a thermal equilibrium is achieved with the same external temperature along the metal plate 30, and the measuring accuracy can be increased.

Since the aim should be to save space with the integration of the sensor unit, especially in ears, the configuration of the thermal insulator 23 and/or the thermal capacitance 24 can be modified. Here the thermal insulator 23 or the capacitance 24 does not have to be arranged on the printed circuit board 22, but can also be incorporated into the latter. Here, for example, a thermal insulator 23 is shown running within the cross-section of the printed circuit board 22, whereby this thermal insulator can be an insulating layer, for example an air pocket. The thermal conductivity is increased by introducing thermovias, for example Cu vias, which are configured as thermal capacitances 24 in the form of blind holes, or through holes, filled with copper. In addition, a thermal capacitance 24 could also be designed as concealed thermovias, so-called "buried vias", which are not shown here.

Figure 2F:
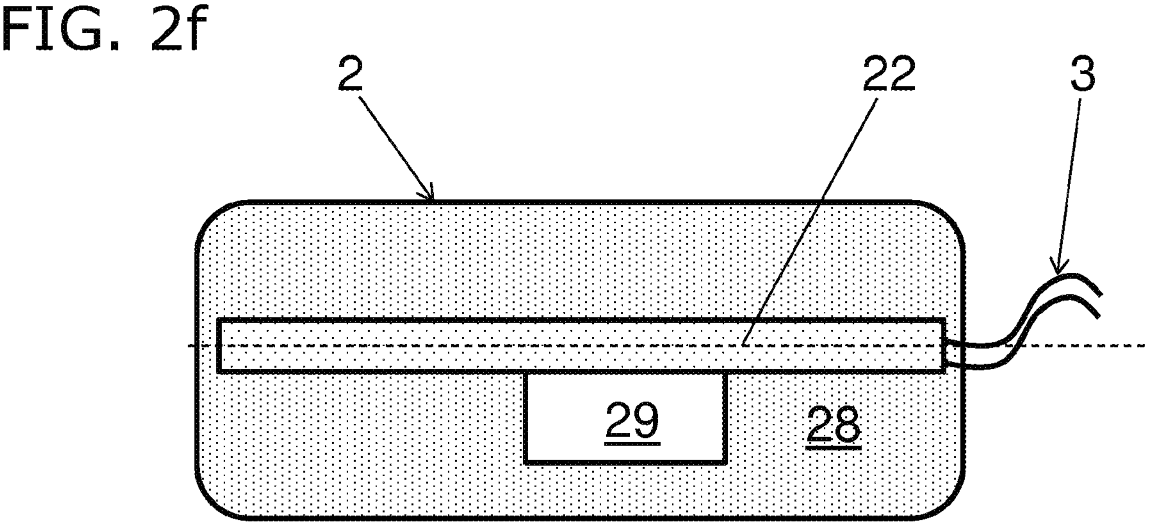
FIG. 2*f* shows a schematic cross-sectional view of a sensor unit, wherein the electronic components, encapsulated in an integrated circuit (IC), are aggregated in a chip housing.

As shown in FIG. 2*f*, the printed circuit board 22, together with the integrated circuit 29, is almost completely surrounded on both sides by the sensor unit sleeve 28. Connection of the connecting wires 3 to the electronics of a portable computer system 0 is readily possible.

Deployable heat flow sensors 20, 20', which in particular can be soldered onto the printed circuit board 22, can be found in EP2938980 and WO2016128247 of the applicant, the contents of which are referenced here. Miniaturised and/or thin monolithic heat flow sensors with low thermal invasiveness can be deployed, which are mechanically sufficiently robust and can be soldered onto the surface of the printed circuit board 22. A sandwich-like structure, consisting of multiple layers of different materials, including metals and at least one electrically insulating matrix layer, is selected for this purpose. Such a monolithic heat flow sensor 20, 20' forms a closed body on at least one side and a number of sensing junctions between different metal layers. Temperature sensors 21 have been of known art for a long time, and variously configured temperature sensors 21 can be used. All temperature sensors 21 of known art that can be soldered onto the printed circuit board 22, or onto another printed circuit board, can be used as the temperature sensors 21. Amongst others, infrared sensors can be used for temperature measurement; these must not be surrounded by a sensor unit sleeve 28. In a preferred embodiment, the sensor unit 2 comprises multiple printed circuit boards 22, whereby the at least one heat flow sensor 20, 20' is arranged on one printed circuit board 22, and an infrared sensor for purposes of temperature measurement is arranged on another printed circuit board, which is arranged spatially separated from the first printed circuit board 22. By means of appropriate wiring, measured values from at least one heat flow sensor 20, 20' on the first printed circuit board 22, and measured values from the infrared sensor on the second printed circuit board, can be processed in the read-out/storage unit 27. Although the infrared sensor is part of the sensor unit 2, it must remain free of the sensor unit sleeve 28. The easiest way to achieve this is to arrange the infrared sensor on the second circuit board.

Figure 3:
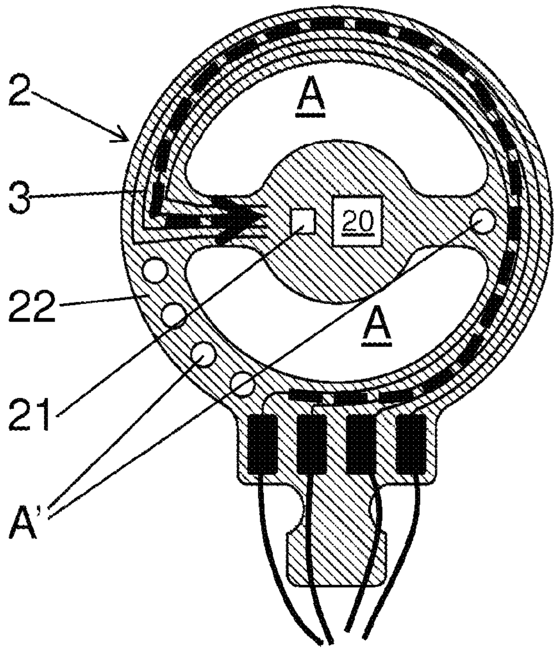
FIG. 3 shows a plan view of a sensor unit before the attachment of a sensor unit sleeve.

FIG. 3 shows a sensor unit 2 with a partially round printed circuit board 22, or more particularly, a partially round cross-sectional area with cavities A in a plan view onto the side of the sensor that subsequently faces the skin surface. For the sake of simplicity, a sensor unit sleeve 28 is omitted here, so that the heat flow and temperature sensors 20, 21 protruding from the side of the sensor are visible. The strip conductors on the printed circuit board 22 run along a circular path that is as long as possible, as indicated by the dashed arrow, along the printed circuit board 22 to the temperature sensor 21 and the heat flow sensor 20 in the centre of the printed circuit board 22. This virtually prevents any thermal heat loss or any interfering heat input caused by heat conduction from the connecting wires 3.

In particular, by the arrangement of the two kidney-shaped cavities A, in each case adjacent in the longitudinal direction to the heat flow and temperature sensors 20, 21, bordering a bridge, whereby a central printed circuit board disk is formed, a thermally-undisturbed mounting of the temperature sensor 21 and the heat flow sensor 20 is achieved. By virtue of the cavities A' in the edge region, any interfering heat flow between the contacts of the connecting wires 3 and the sensors 20, 21 is also further reduced.

Figure 4A:
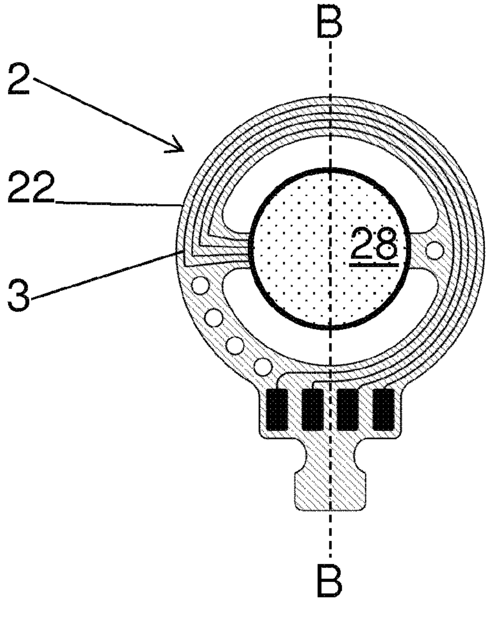
Figure 4B:
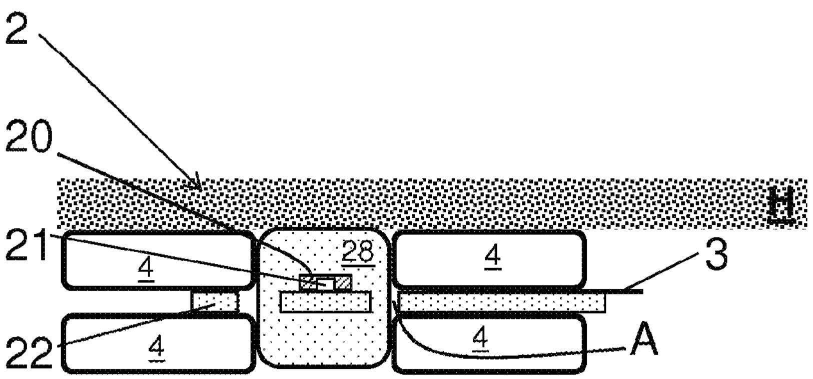
FIG. 4*b* shows a schematic cross-sectional view of the sensor unit shown in FIG. 4*a* along the B-B cross-sectional line.
Figure 5:
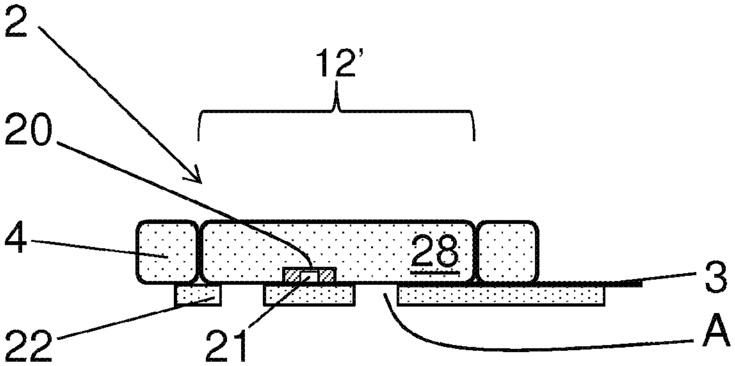
FIG. 5 shows a schematic cross-sectional view of a sensor unit with a sensor unit sleeve in a cavity in an adhesive pad.

A sensor unit 2 fitted with a sensor unit sleeve 28 is shown in FIG. 4*a*. The sensor unit sleeve 28 partially covers the electrical components and the printed circuit board 22. When in use, as shown in FIG. 4*b* along the cross-sectional line B-B, the sensor unit 2 with its sensor unit sleeve 28 is laid or pressed onto the skin H of a user, and the measurement of heat flows and temperatures can thus take place, and the current core body temperature can be determined using algorithms of known art. Here the sensor unit sleeve 28 also extends onto the side of the printed circuit board 22 facing away from the skin, and the sensor unit sleeve 28 is surrounded by an adhesive pad 4.

After the manufacture of the sensor unit 2 with the sensor unit sleeve 28 attached, the printed circuit board 22 together with the protruding sensor unit sleeve 28 can be attached in a cavity 12' of the adhesive pad 4, which is of known art from medical technology, and serves, for example, for the attachment of electrodes to the skin. The connecting wires 3 can be connected to the electronics of a medical device, either before or after the attachment of the sensor unit 2 in the adhesive pad 4. The adhesive pad 4 is manufactured from the same materials as the thermal insulator 23 and has an adhesive layer that is compatible with the skin, e.g. as is of known art from the company 3M.

The thermal conductivity $\lambda$ of the material of the thermal adhesive pad 4 should be of the order of that for air ($\lambda_{air}$=0.024 W/m/K), i.e. between 0.01 W/m/K and 0.1 W/m/K.

In order to introduce the sensor unit 2 as easily as possible into a housing 1 of a portable computer system the following methods are used.

Preferred Manufacturing and Integration Method

Figure 6A:
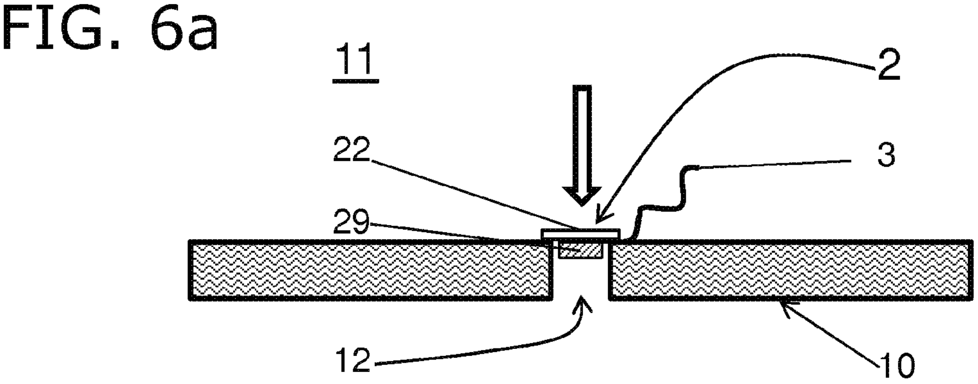
Figure 6B:
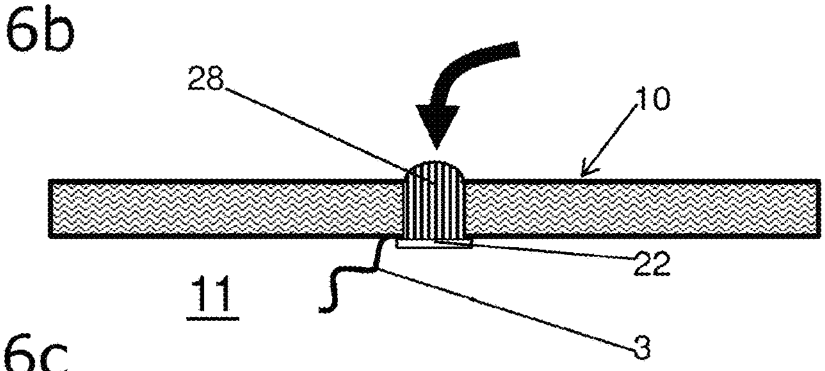
FIG. 6*b* shows a schematic cross-sectional view of the sensor unit after the filling of a through hole.
Figure 6C:
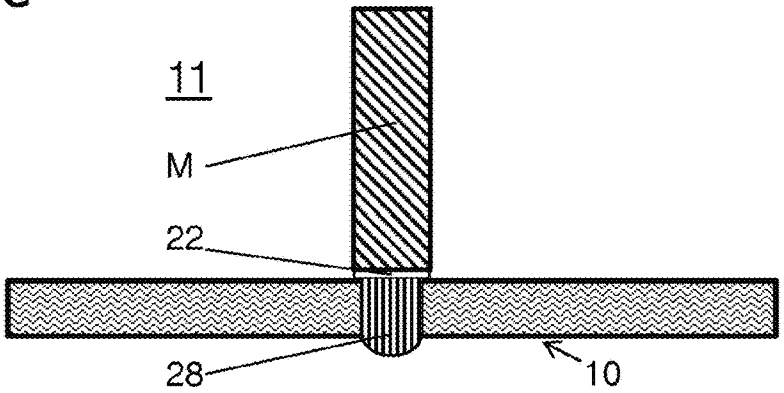
FIG. 6*c* shows a schematic cross-section after the attachment of a metal rod to the sensor unit.

FIG. 6 show a method for the integration of a sensor unit 2 into a housing 1 of a portable computer system A sensor unit 2 is used to cover a through hole 12 in the housing 1 in such a way that the edges of the printed circuit board 22 close off the through hole 12. Here the electronic components such as the heat flow sensor 20 and the temperature sensor 21, are positioned at the height of the through hole 12, or protrude into the through hole 12. The printed circuit board 22 can be bonded to the walls of the housing 1 by means of adhesive. As a result of covering the through hole 12 with the printed circuit board 22, in a further step the through hole 12 can be filled, for example with a silicone mass, so as to form the sensor unit sleeve 28. Here, the filling in FIG. 6*b* is executed in such a way that a part of the sensor unit sleeve 28 protrudes from the through hole 12 in the direction of the skin contact side 10. The positioning of the printed circuit board 22 is carried out as indicated by the arrow. The sensor unit 2 is executed as described above, but is only fitted with the sensor unit sleeve 28 after the printed circuit board 22 has been fixed in place. The through hole 12 is filled from the direction of the interior 11 of the housing 1.

The connecting wires 3 from the printed circuit board 22 to the electronics (not shown) can either be connected before the casting or filling process, or only after the cavity 12 has been filled.

In order to obtain accelerated heat conduction, and to maintain an equilibrium between the environment and the body, a metal rod M, which crosses the interior 11 of the housing 1 and is in contact with the exterior of the housing 1, is attached onto the side of the printed circuit board 22 facing away from the body, pointing in the direction of the interior 11 and at the height of the heat flow sensor 20. Depending on the embodiment, this metal rod M can also be thermally insulated on its side walls.

Figure 7A:
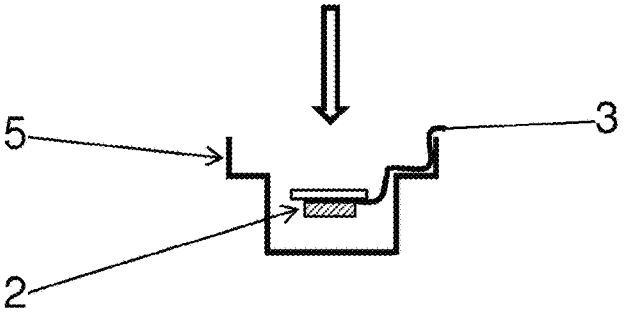
Figure 7B:
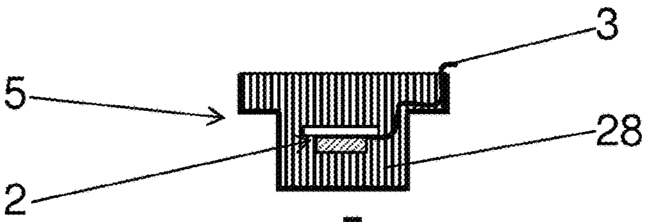
FIG. 7*b* shows a schematic cross-sectional view of a sensor unit encapsulated in a sensor unit sleeve.
Figure 7C:
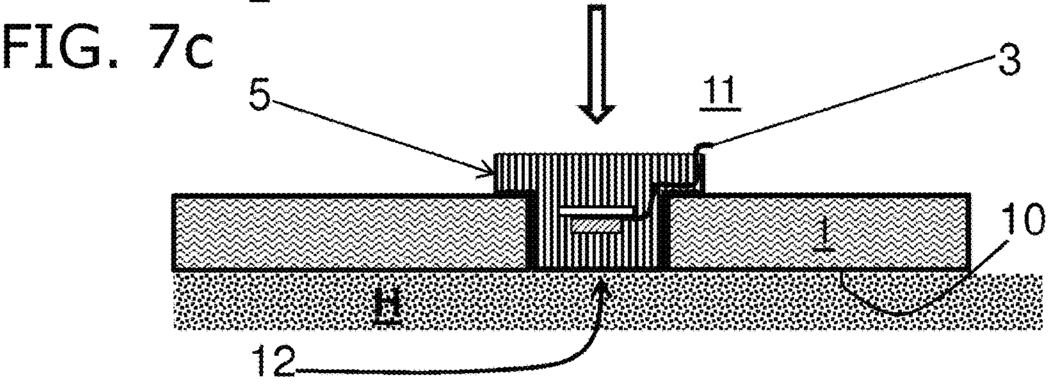
FIG. 7*c* shows a schematic cross-sectional view of the encapsulated sensor unit shown in FIG. 6*b*, after it has been pressed into a cavity in a housing of a portable computer system, and has been brought into contact with the skin of a user.

It is also possible to use another manufacturing method, which is described in FIGS. 7*a* to 7*c*. After the manufacture of the sensor unit 2, it is placed in a casting mould 5, whereby the connecting wires 3 protrude from the casting mould 5. The walls of the casting mould 5 can be made either from metal or a plastic material.

In the next step, the casting mould 5 is filled with a material that later forms the sensor unit sleeve 28. The sensor unit 2 is enclosed by the material on all sides, such that the printed circuit board 22 and all components are enclosed by the sensor unit sleeve 28. After curing, the enclosed sensor unit 2 can be placed in a cavity 12, 13 in the housing 1 of a portable computer system 0, and pressed into it in a detachably held manner. The thermally sufficiently conductive material of the sensor unit sleeve 28 makes close contact with the walls of the cavity 12, 13, which prevents it from slipping out unintentionally. The sensor unit 2 embedded in the sensor unit sleeve 28 forms a plug, which remains in the cavity 12, 13.

To improve the retention, a suitable adhesive can be used, which is distributed over the walls of the cavity 12, 13 before the sensor unit 2 encased in the sensor unit sleeve 28 is pressed in. Correspondingly, a non-detachable connection can also be achieved.

The casting mould 5 used here can optionally be used as a lost mould, can remain connected to the sensor unit 2, or can be removed before the sensor unit 2 is mounted in the cavity 12 in the housing 1.

In practice, when the sensor unit 2 is placed on the skin H, measured values from the at least one heat flow sensor 20, 20' and the at least one temperature sensor 21, 21' are recorded, from which the core body temperature can be determined, using a variety of algorithms. Calibration measurements are necessary for the most accurate determinations possible, and the types and thicknesses of the materials used must be known. Multiple possible algorithms are of known art, which lead to useful results in the determination of the core body temperature.

The sensor unit 2 is preferably inserted into the sensor unit sleeve 28 in such a way that the sensor unit sleeve 28 is partially arranged so as to protrude from the housing 1, away from the walls of the housing 1. The thermal coupling of the sensor unit 2, or more particularly, the sensors 20, 21, is then optimised accordingly.

The sensor unit sleeve 28 could be a sleeve or a cylinder made from PVC, for example, which is filled with the thermally conductive material. This cylinder could also be made of an insulating material (foam), so as to better define the thermal path.

In one variant, the sensor unit 2 can have multiple printed circuit boards 22, separated from one another, on which temperature sensors 21, 21' and heat flow sensors 20, 20' and/or other electronic components can be arranged, separated from one another. All the printed circuit boards 22 should then be at least partially surrounded by at least one sensor unit sleeve 28. If an infrared sensor is used as the temperature sensor 21, 21', it must not be surrounded by the sensor unit sleeve 28.

LIST OF REFERENCE SYMBOLS

- 0 Portable computer system
- 1 Housing
  - 10 Skin contact side
  - 11 Interior
  - 12 Cavity/through hole
  - 13 Cavity/blind hole
- 2 Sensor unit
  - 20, 20' Heat flow sensor (at least 1)
  - 21, 21' Temperature sensor (at least 1)
  - 22 Printed circuit board, PCB
  - 23 Thermal insulator
  - 24 Thermal capacitance
  - 25 Analogue-to-digital converter
  - 26 Microcontroller
  - 27 Read-out/storage unit
  - 28 Sensor unit sleeve
  - 29 Integrated switching circuit, packaged
  - 30 Metal plate
  - A Cavity
- 3 Connecting cable (to the electronics)
- 4 Adhesive pad (to be attached to the skin)
- 5 Casting mould

The invention claimed is:

1. The manufacture of portable computer system with a sensor unit for determining the core body temperature, by integration of the sensor unit comprising:

one or more heat flow sensors, in the form of a solderable thin monolithic heat flow sensor with sandwich-like structure, forming a closed body on at least one side and a number of sensing junctions between different metal layers, at least one measuring temperature sensor, wherein the at least one measuring temperature sensors and the one or more heat flow sensors are soldered directly onto a printed circuit board or onto two different printed circuit boards, into a housing or into an adhesive pad, to be attachable onto a skin (H) of a user, wherein:

provision of the housing with a cavity, or the adhesive pad with a cavity, provision of the sensor unit insertion of the sensor unit into a sensor unit sleeve of a mechanically flexible material comprising a thermally conductive silicone, wherein connecting wires protrude from the sensor unit sleeve, insertion of the sensor unit at least partly enclosed by the sensor unit sleeve into the cavity in the housing of the portable computer system, or the cavity in the adhesive pad, and subsequent connection of the connecting wires to the electronics of the portable computer system, wherein the sensor unit is embedded in the sensor unit sleeve forming a plug which remains in a recess of the housing.

2. According to claim 1, where the sensor unit sleeve comprises a cured thermally conductive material.

3. According to claim 1 where the sensor unit sleeve is a thermally conductive pad.

4. The method in accordance with claim 1, wherein the integrated sensor unit comprises two printed circuit boards, and the at least one heat flow sensor and the at least one temperature sensor are arranged on different printed circuit boards that are spatially separated.

5. The method in accordance with claim 1, wherein the at least one printed circuit board of the integrated sensor unit with the temperature sensor remains at least partially free of the sensor unit sleeve.

6. The method in accordance with claim 1, wherein the at least one monolithic heat flow sensor and the at least one temperature sensor of the integrated sensor unit are soldered layered on top of one another, onto the same side of the at least one printed circuit board of the integrated sensor unit.

7. The method in accordance with claim 1, wherein an analogue-to-digital converter, a microcontroller and a read-out/storage unit are arranged directly attached onto the at least one printed circuit board of the integrated sensor unit.

8. The method in accordance with claim 6, wherein the at least one monolithic heat flow sensor, the at least one temperature sensor, the analogue-to-digital converter, the microcontroller, a thermal insulator, and/or a thermal capacitance, packaged in an integrated circuit, are attached onto one side of the at least one printed circuit board of the integrated sensor unit.

9. The method in accordance with claim 1, wherein two heat flow sensors are soldered onto the same side of the at least one printed circuit board of the integrated sensor unit, spaced apart from one another in the longitudinal direction, and a thermal insulator is arranged on the side of the printed circuit board that is free of heat flow sensors, at the height of the first heat flow sensor in the longitudinal direction, such that a first heat flow can be measured through the thermal insulator and the first heat flow sensor, and a second heat flow can be measured through the second heat flow sensor.

10. The method in accordance with claim 1, wherein two heat flow sensors are soldered onto the same side of the at least one printed circuit board of the integrated sensor unit, spaced apart from one another in the longitudinal direction, and a thermal capacitance is arranged on the side of the at least one printed circuit board that is free of heat flow sensors, at the height of the first heat flow sensor in the longitudinal direction, such that a first heat flow can be measured through the thermal capacitance and the first heat flow sensor, and a second heat flow can be measured through the second heat flow sensor.

11. The method in accordance with claim 1, wherein on the side of the at least one printed circuit board of the integrated sensor unit that is free of heat flow sensors a metal plate is arranged so as to be extensively in contact with a thermal insulator, and/or a thermal capacitance, and/or a block made from a thermally conductive material, and/or a part of the sensor unit sleeve.

12. The method in accordance with claim 1, wherein on one side of the at least one printed circuit board of the integrated sensor unit, a heat flow sensor, a first temperature sensor, and a thermal insulator are spaced apart from one another in the longitudinal direction, and on the opposite side of the at least one printed circuit board that is free of heat flow sensors a second temperature sensor is arranged at the height of the thermal insulator along the longitudinal direction, such that a first temperature can be measured at the location of the first temperature sensor, and a second temperature can be measured at the location of the second temperature sensor after passage of the heat flow through thermal insulator.

13. The method in accordance with claim 1, wherein the casting mould remains as a lost mould on the material of the sensor unit sleeve.

14. The method in accordance with claim 1, wherein the casting mould is removed from the sensor unit sleeve after the curing of the latter.

15. The method in accordance with claim 1, wherein the cavity is designed as a through hole.

16. The method in accordance with claim 1, wherein the cavity is designed as a blind hole.

17. The method in accordance with claim 1, wherein the sensor unit sleeve is mechanically flexible, and the thermal conductivity lies between 0.3 and 10 W/mK, preferably between 0.8 and 3 W/mK, preferably manufactured from a thermally conductive silicone.

18. The method in accordance with claim 1, wherein the inner walls of the cavities are coated with an adhesive, before the sensor unit sleeve, or the sensor unit sleeve encased by the casting mould, is plugged into the cavity.

19. The method in accordance with claim 1, wherein the cross-sectional area of the at least one printed circuit board of the integrated sensor unit is at least partially circular, and strip conductors are guided at least partially along circular lines to the centre of the at least one printed circuit board, wherein the soldering surfaces of the at least one heat flow sensor and of the at least one temperature sensor are located in the centre of the at least one printed circuit board.

20. The method in accordance with claim 1, wherein wherein the centre of the at least one printed circuit board is surrounded by PCB-cavities (A) and both PCB-cavities (A) are arranged adjacent in the longitudinal direction to the heat flow and temperature sensors, bordering a bridge and a central printed circuit board disk is formed.

21. The method in accordance with claim 19, wherein the PCB-cavities (A) are executed as kidney shapes.

22. The method in accordance with claim 19, wherein with PCB-cavities (A') in the edge region of the at least one printed circuit board, any interfering heat flow between the contacts of the connecting wires and the sensors is reduced.

* * * * *